(12) United States Patent
Kito et al.

(10) Patent No.: US 7,729,475 B2
(45) Date of Patent: Jun. 1, 2010

(54) RADIATION IMAGE CAPTURING APPARATUS

(75) Inventors: Eiichi Kito, Minami-ashigara (JP); Sadato Akahori, Odawara (JP); Kazuharu Ueta, Tokyo (JP); Yasunori Ohta, Yokohama (JP); Atsushi Fukuda, Koganei (JP)

(73) Assignee: FUJIFILM Corporation, Tokyo (JP)

( * ) Notice: Subject to any disclaimer, the term of this patent is extended or adjusted under 35 U.S.C. 154(b) by 55 days.

(21) Appl. No.: 12/239,273

(22) Filed: Sep. 26, 2008

(65) Prior Publication Data

US 2009/0086887 A1 Apr. 2, 2009

(30) Foreign Application Priority Data

Sep. 28, 2007 (JP) ............................ 2007-2551330

(51) Int. Cl.
*H05G 1/28* (2006.01)
(52) U.S. Cl. .......................... 378/162; 378/63; 378/163; 378/204
(58) Field of Classification Search ................... 378/62, 378/63, 162, 163, 204, 207; 382/132
See application file for complete search history.

(56) References Cited

U.S. PATENT DOCUMENTS 7,396,161 B2 * 7/2008 Schmitt ...................... 378/204

FOREIGN PATENT DOCUMENTS

| JP | 07-265286 A | 10/1995 |
|---|---|---|
| JP | 09-311187 A | 12/1997 |
| JP | 2003-151795 A | 5/2003 |
| JP | 2005-192856 A | 7/2005 |

* cited by examiner

*Primary Examiner*—Jurie Yun
(74) *Attorney, Agent, or Firm*—Sughrue Mion, PLLC

(57) ABSTRACT

A radiation image capturing apparatus that includes a radiation conversion panel comprises an input device for inputting a first distance from the position of the panel to a position serving as a reference position for a subject, a distance measuring unit for measuring a second distance from the radiation source to the panel, a first radiation field calculating unit for determining a radiation field at the position of the panel based on setting information of the radiation source and the second distance, a second radiation field calculating unit for determining a hypothetical radiation field at the reference position of the subject based on the setting information of the radiation source, the first distance, and the second distance, and a life-size correcting unit for correcting the radiation image information from the panel based on the information of the calculated radiation field and the information of the calculated hypothetical radiation field.

6 Claims, 10 Drawing Sheets

RADIATION IMAGE CAPTURING APPARATUS

BACKGROUND OF THE INVENTION

1. Field of the Invention

The present invention relates to a radiation image capturing apparatus including a radiation source and a radiation conversion panel for detecting radiation emitted from the radiation source, which has passed through a subject, and converting the detected radiation into radiation image information.

2. Description of the Related Art

Radiation image capturing apparatuses having a radiation conversion panel for detecting radiation emitted from a radiation source that has passed through a subject and converting the detected radiation into radiation image information are disclosed in Japanese Laid-Open Patent Publication No. 09-311187, Japanese Laid-Open Patent Publication No. 07-265286, Japanese Laid-Open Patent Publication No. 2003-151795, and Japanese Laid-Open Patent Publication No. 2005-192856, for example.

Specifically, Japanese Laid-Open Patent Publication No. 09-311187 discloses a nuclear medicine image diagnostic apparatus for displaying a life-sized radioactive material distribution image of a subject in the same position as the subject. In the nuclear medicine image diagnostic apparatus, radiation applied from a collimator mounted on a rear surface of the apparatus is detected by a semiconductor detector, and positions where radiation is applied are successively calculated and stored by a processor, and then displayed on a liquid crystal display panel mounted on a front surface of the apparatus.

Japanese Laid-Open Patent Publication No. 07-265286 discloses an X-ray diagnostic apparatus, which also is capable of outputting a life-sized image. The disclosed X-ray diagnostic apparatus comprises an X-ray tube, a top plate, an image intensifier, a TV camera for capturing an optical image from the image intensifier, and an output device for outputting the image captured by the TV camera. The X-ray diagnostic apparatus also includes an SID measuring unit for measuring a distance (SID) from the X-ray tube to the X-ray irradiated surface of the image intensifier, and an FSD measuring unit for determining a distance (FSD) from the center of a subject to the X-ray irradiated surface of the image intensifier. Based on the SID and the FSD, the X-ray diagnostic apparatus determines an enlargement ratio and outputs the captured image in full scale. The FSD measuring unit estimates the FSD based on detected values from a sensor for detecting the vertical position of the top plate and a sensor for detecting the vertical position of the image intensifier, and the small distance between the subject and the top plate.

Japanese Laid-Open Patent Publication No. 2003-151795 discloses an X-ray image capturing apparatus for easily generating quasi-parallel X-rays to obtain a life-sized image of a subject. The X-ray image capturing apparatus operates as follows: X-rays are output through a window. After an X-ray radiation field is limited by a diaphragm, the X-rays are applied to a flat polycapillary plate, which produces parallel X-rays. The parallel X-rays are applied to the subject to generate an image of the subject on an imaging plate. Because parallel X-rays are used, the generated image produces a life-sized image of the subject.

Japanese Laid-Open Patent Publication No. 2005-192856 discloses that the distance from the front surface of an X-ray image intensifier that makes up an X-ray detector to the affected area of a subject is set to a desired distance. The distance from the position of an image-capturing surface to the reference position of the subject also is entered. The publication further discloses a life-sized image data correction technique, based on calculating a magnification ratio using the distance between the front surface of the X-ray detector and the affected area of the subject.

The apparatuses disclosed in Japanese Laid-Open Patent Publication No. 09-311187 and Japanese Laid-Open Patent Publication No. 2003-151795 are disadvantageous in that they are large in size and costly to manufacture, due to the fact that a collimator means is required for optically converting the radiated X-rays into parallel X-rays.

According to the X-ray diagnostic apparatus disclosed in Japanese Laid-Open Patent Publication No. 07-265286, the FSD is determined based on the top plate as a reference. However, the reference provided by the top plate tends to fluctuate, since the top plate may warp under the weight of the subject that is supported by the top plate. In addition, a preset fixed value is used as the distance between the central position of the subject and the top plate. However, the distance between the central position of the subject and the top plate may change greatly, depending on the physique of the subject. Consequently, the X-ray diagnostic apparatus disclosed in Japanese Laid-Open Patent Publication No. 07-265286 fails to convert the acquired image into a life-sized image accurately.

According to Japanese Laid-Open Patent Publication No. 2005-192856, the distance from the position of the image-capturing surface to the reference position of the subject can be set to an arbitrary distance. However, no consideration is given to facilitating acquisition of life-sized image information from the radiation conversion panel at an arbitrary position, based on the radiation image information that has already been acquired, for thereby shortening medical procedures that are performed using the radiation image capturing apparatus. Furthermore, although the image corresponding to the reference position is corrected to provide a life-sized image, images of other regions of the subject are of sizes that are different from the actual size of the subject. If the operator is not certain as to whether the image displayed on the display monitor has been corrected to provide a life size or not, then the operator possibly could misidentify the size and position of the region of the subject in question.

SUMMARY OF THE INVENTION

It is an object of the present invention to provide a radiation image capturing apparatus, which is capable of easily acquiring life-sized image information from a radiation conversion panel at an arbitrary position, based on radiation image information that has already been acquired, for thereby shortening the medical procedures that are performed using the radiation image capturing apparatus.

Another object of the present invention is to provide a radiation image capturing apparatus, which allows the operator to recognize at a glance whether an image displayed on a display monitor is an image from the radiation conversion panel, or an image that has been corrected to provide a life-sized representation, for thereby preventing the operator from misidentifying the size and position of the region of the subject in question.

A radiation image capturing apparatus according to the present invention comprises a radiation source, a radiation conversion panel for detecting radiation emitted from the radiation source and that has passed through a subject and converting the detected radiation into radiation image information, an input device for inputting at least a first distance from a position of the radiation conversion panel to a position serving as a reference position of the subject, a distance measuring unit for measuring a second distance from the radiation source to the radiation conversion panel, a first radiation field calculating unit for determining a radiation field at the position of the radiation conversion panel based on setting information of the radiation source and the second distance, a second radiation field calculating unit for determining a hypothetical radiation field at the reference position of the subject based on the setting information of the radiation source, the first distance, and the second distance, and a life-size correcting unit for correcting the radiation image information from the radiation conversion panel to provide life-sized image information based on the information of the calculated radiation field and the information of the determined hypothetical radiation field.

The radiation image capturing apparatus may further comprise an output unit for outputting the life-sized image information from the life-size correcting unit.

The radiation image capturing apparatus may further comprise an editing unit for editing at least one of message information indicating that the radiation image information has been corrected to provide the life-sized image information from the life-size correcting unit, the information of the first distance, and information indicative of the reference position of the subject, to thereby provide edited image information, and an output unit for outputting the edited image information from the editing unit.

Consequently, the operator of the radiation image capturing apparatus can recognize at a glance whether an image displayed on a display monitor is an image taken directly from the radiation conversion panel, or an image that has been converted into a life-sized image. The operator therefore is prevented from misidentifying the size and position of the region of the subject in question.

The input unit may comprise an image capturing unit for capturing an image of the radiation conversion panel and the subject, and a distance calculating unit for calculating the first distance based on captured image information from the image capturing unit.

The radiation image capturing apparatus may further comprise an image capturing unit for capturing an image of the radiation conversion panel and the subject, a marker adding unit for adding marker information indicative of the position serving as the reference position of the subject, which is spaced from the position of the radiation conversion panel by the first distance, the marker information being added to captured image information from the image capturing unit, an editing unit for editing at least one of message information indicating that the radiation image information has been corrected to provide the life-sized image information from the life-size correcting unit, the information of the first distance, and the information indicative of the reference position of the subject, and the captured image information to which the marker information has been added, to thereby provide edited image information, and an output unit for outputting the edited image information from the editing unit.

The radiation image capturing apparatus may further comprise a cassette having a casing, the radiation conversion panel being housed in the casing, the casing including a side wall bearing thereon a marker indicative of an installation position of the radiation conversion panel.

According to the present invention, as described above, since the radiation image capturing apparatus can easily produce life-sized image information at an arbitrary position from the radiation conversion panel, based on radiation image information that has already been acquired, medical procedures that are performed using the radiation image capturing apparatus can effectively be shortened.

In addition, the operator can recognize at a glance whether an image displayed on a display monitor is an image taken directly from the radiation conversion panel or an image that has been converted into a life-sized image. The operator is thus prevented from misidentifying the size and position of the region of the subject in question.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Like or corresponding parts of the present invention are denoted by like or corresponding reference characters throughout the views.

Radiation image capturing apparatuses according to embodiments of the present invention will be described below with reference to FIGS. 1 through 10.

Figure 1:
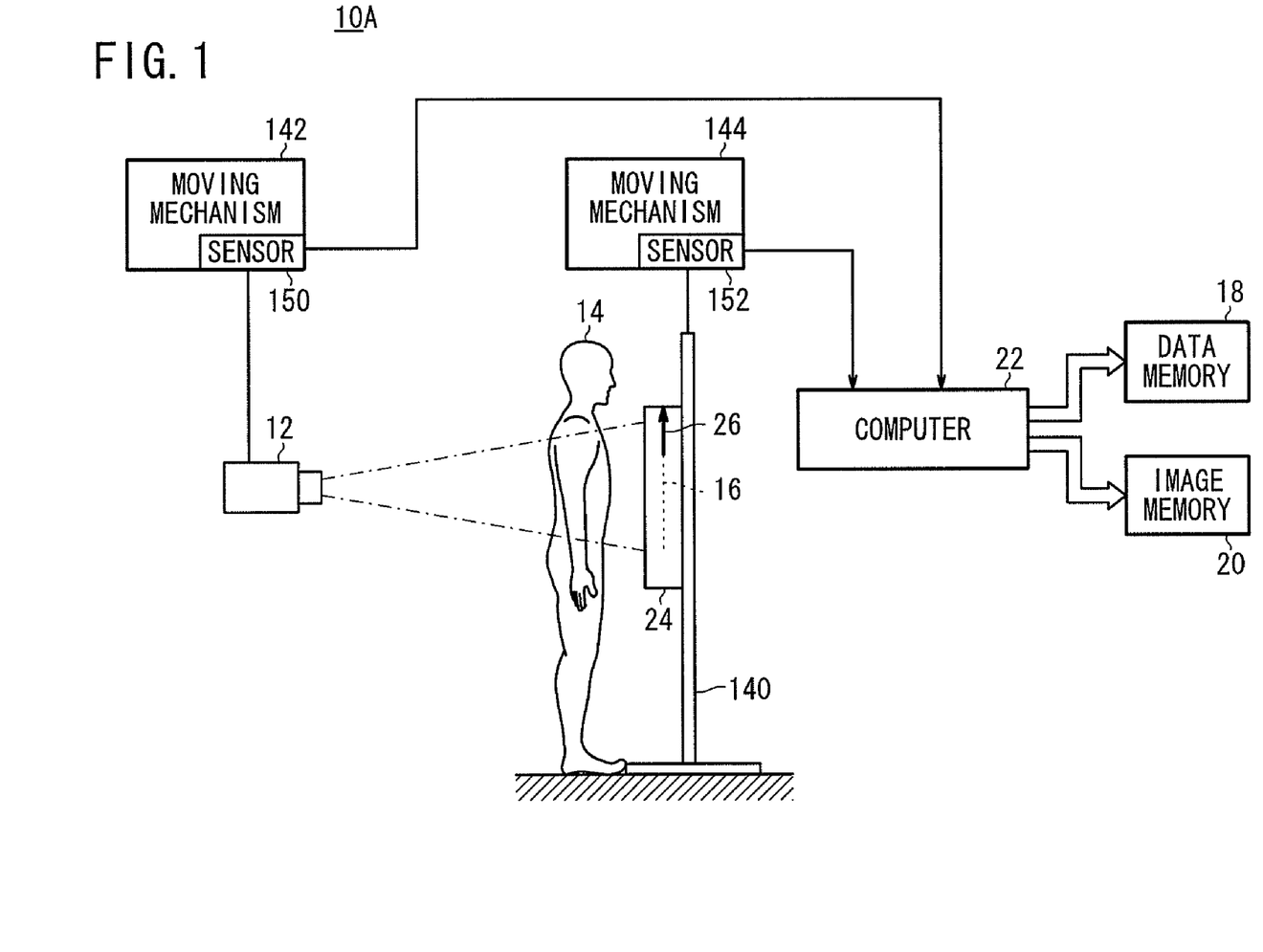
FIG. 1 is a block diagram of a first radiation image capturing apparatus according to the present invention, which is arranged to operate in a first mode.

As shown in FIG. 1, a radiation image capturing apparatus 10A according to a first embodiment of the present invention (hereinafter referred to as a "first radiation image capturing apparatus 10A") comprises a radiation source 12, a radiation conversion panel 16 for detecting radiation emitted from the radiation source 12 and having passed through a subject 14, and converting the detected radiation into radiation image information, a data memory 18 for registering various parameters, an image memory 20 for storing radiation image information, and a computer 22 for controlling various means and components of the first radiation image capturing apparatus 10A.

The radiation conversion panel 16 is housed in a casing of a cassette 24. A marker 26 indicative of the installation position of the radiation conversion panel 16 is applied to a side wall of the casing. When the cassette 24 is set in the first radiation image capturing apparatus 10A, the marker 26 on the side wall of the casing allows the operator to easily recognize the position of the radiation conversion panel 16.

Figure 2:
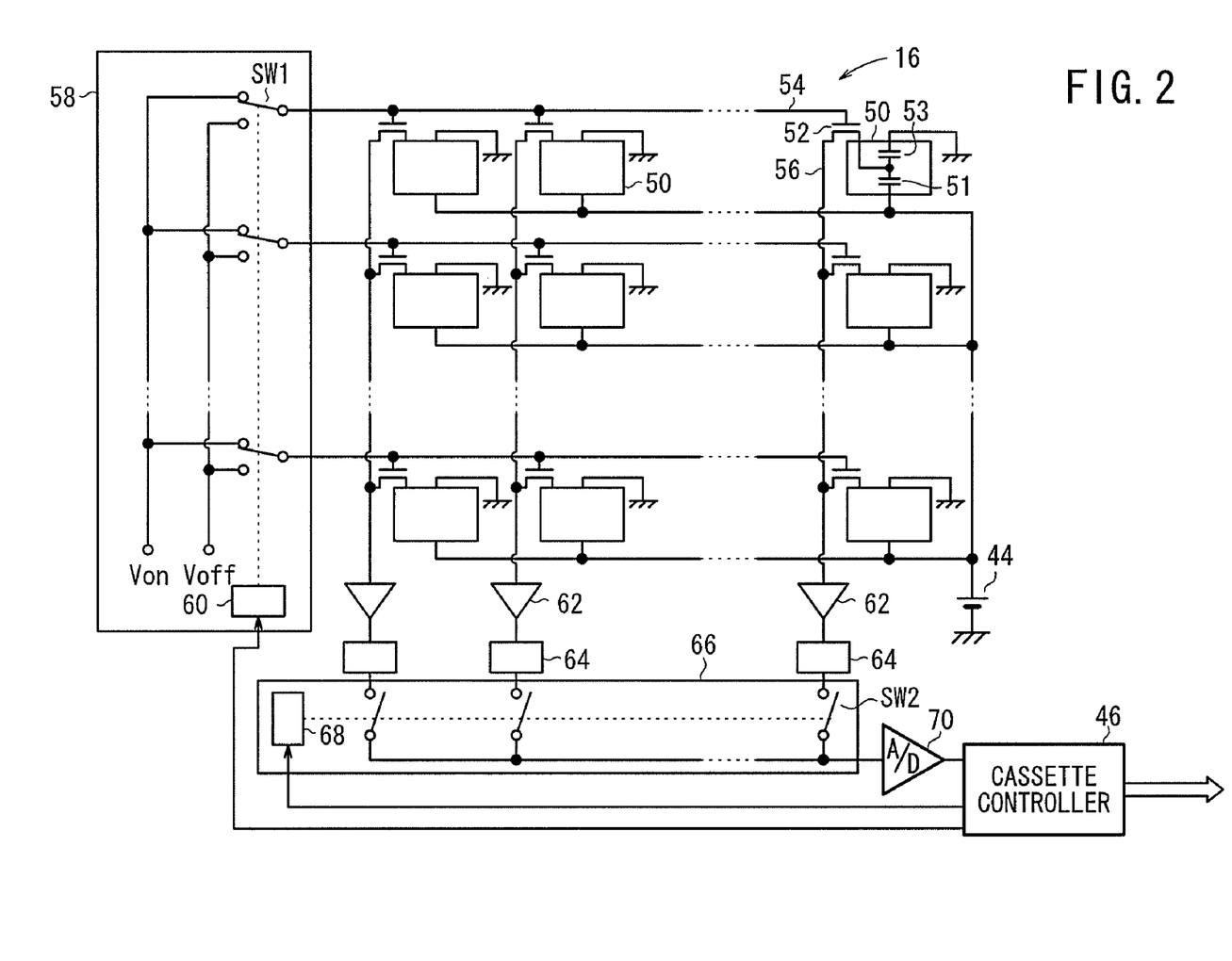
FIG. 2 is a block diagram of a circuit arrangement of a radiation conversion panel.
Figure 3:
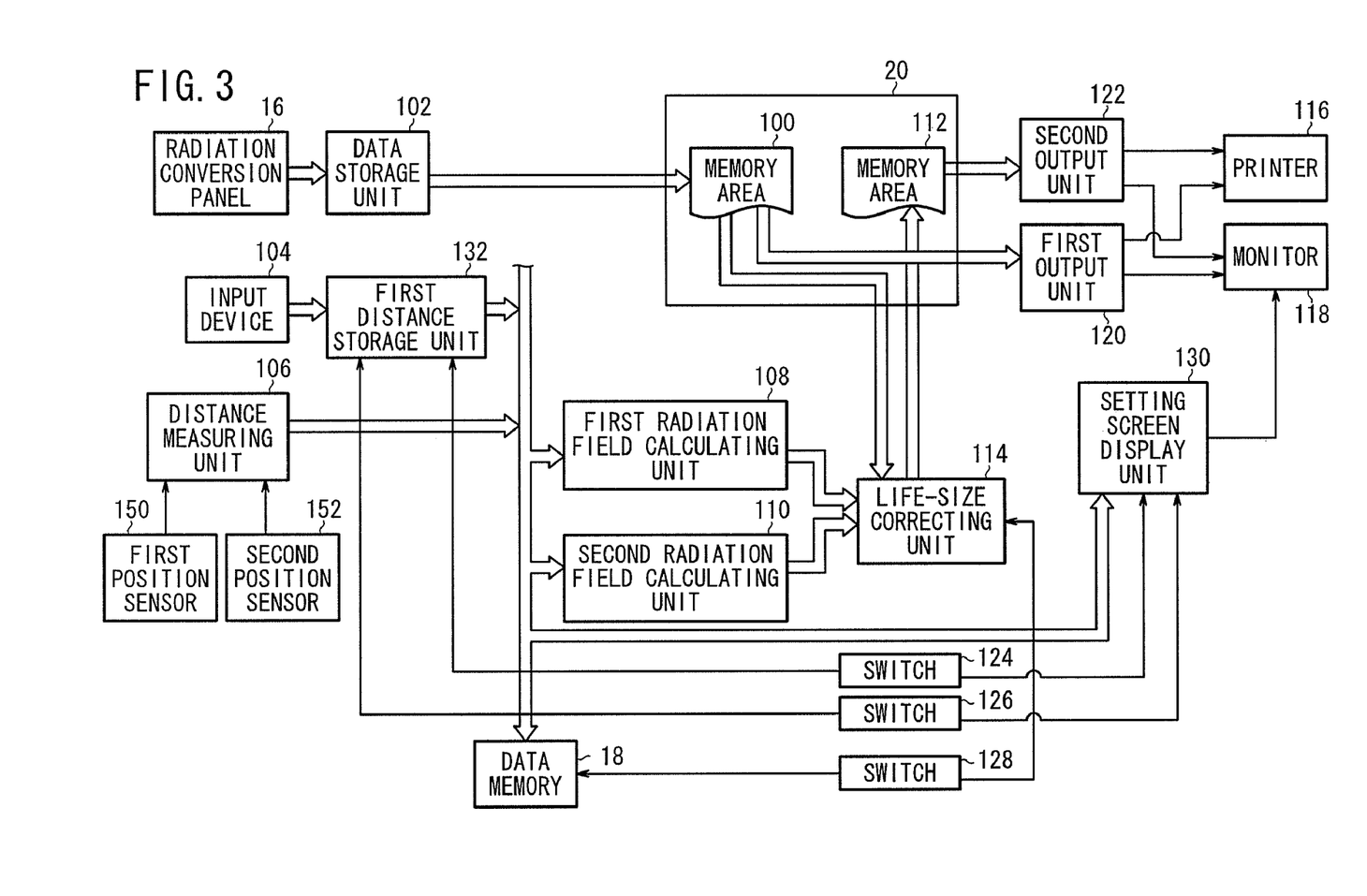
FIG. 3 is a functional block diagram of a control system of the first radiation image capturing apparatus.

As shown in FIG. 2, the radiation conversion panel 16 comprises an array of thin-film transistors (TFTs) 52 arranged in rows and columns, a photoelectric conversion layer 51 made of a material such as amorphous selenium (a-Se) for generating electric charges upon detection of radiation. The photoelectric conversion layer 51 is disposed on the array of TFTs 52. An array of storage capacitors 53 is connected to the photoelectric conversion layer 51. When radiation X is applied to the radiation conversion panel 16, the photoelectric conversion layer 51 generates electric charges, and the storage capacitors 53 store the generated electric charges. Then, the TFTs 52 are turned on, each row at a time, to read the electric charges from the storage capacitors 53 as an image signal. In FIG. 3, the photoelectric conversion layer 51 and one of the storage capacitors 53 are shown as making up a pixel 50, wherein the pixel 50 is connected to one of the TFTs 52. Details of the other pixels 50 are omitted from illustration. Since amorphous selenium tends to change in structure and lose functions thereof at high temperatures, amorphous selenium needs to be used within a certain temperature range. Therefore, some means for cooling the radiation conversion panel 16 should preferably be provided in the cassette 24.

The TFTs 52 connected to the respective pixels 50 are connected to respective gate lines 54 extending parallel to the rows, and to respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff for turning on and off the TFTs 52 along the rows from the line scanning driver 58. The line scanning driver 58 comprises a plurality of first switches SW1 for switching between the gate lines 54. and an address decoder 60 for outputting a selection signal for selecting one of the first switches SW1 at a time. The address decoder 60 is supplied with an address signal from the cassette controller 46.

The signal lines 56 are supplied through the TFTs 52, which are arranged in columns, with electric charges stored in the storage capacitors 53 of the pixels 50. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of second switches SW2 for successively switching between the signal lines 56, and an address decoder 68 for outputting a selection signal for selecting one of the second switches SW2 at a time. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing the radiation image information, which is supplied to the cassette controller 46. The cassette controller 46 supplies the digital image signal to the computer 22, which stores the digital image signal, i.e., the radiation image information, in the image storage memory 20.

As shown in FIG. 3, the first radiation image capturing apparatus 10A comprises a data storage unit 102 for storing radiation image information from the radiation conversion panel 16 in a first memory area 100 of the image memory 20, an input device 104 for inputting a first distance from the position of the radiation conversion panel 16 to a position that serves as a reference position for the subject 14, a distance measuring unit 106 for measuring a second distance from the radiation source 12 to the radiation conversion panel 16, a first radiation field calculating unit 108 for determining a radiation field at the position of the radiation conversion panel 16 based on setting information of the radiation source 12 and the second distance, a second radiation field calculating unit 110 for determining a hypothetical radiation field at the reference position of the subject 14 based on the setting information of the radiation source 12, the first distance, and the second distance, a life-size correcting unit 114 for correcting the radiation image information from the radiation conversion panel 16 so as to provide life-sized image information based on the information of the calculated radiation field and the information of the calculated hypothetical radiation field, and storing the life-sized image information in a second memory area 112 of the image memory 20, a first output unit 120 for reading radiation image information from the first memory area 100 of the image memory 20 and outputting the read radiation image information to a printer 116 and to a display monitor 118, and a second output unit 122 for reading the life-sized image information from the second memory area 112 of the image memory 20 and outputting the read life-sized radiation image information to the printer 116 and to the display monitor 118.

The first distance that is input from the input device 104 may be of an arbitrary value. Preferably, however, the first distance is selected as a distance from the position of the radiation conversion panel 16 in the cassette 24, which is placed in the first radiation image capturing apparatus 10A, to an arbitrary position on the side of the subject 14. The arbitrary position on the side of the subject 14, which is indicated by the first distance, is used as the reference position for the subject 14.

The reference position of the subject 14 may be set empirically on a shoulder bone of the subject 14. In this case, the distance from the position of the radiation conversion panel 16 to the shoulder bone of the subject 14 is measured, and the measured distance is input as a reference position via the input device 104.

As shown in FIG. 3, the first radiation image capturing apparatus 10A further includes a default value setting switch 124, a correction request switch 126 for requesting a change or correction of the first distance, and a correction execution switch 128 for performing a life-size correction. These switches 124, 126, 128 are mounted on a control console.

The first radiation image capturing apparatus 10A also includes a setting screen display unit 130 for displaying a setting screen on the display monitor 118, based on operations of the default value setting switch 124 and the correction request switch 126, and a first distance storage unit 132 for storing the first distance input from the input device 104 in a corresponding memory area of the data memory 18, based on operations of the default value setting switch 124 and the correction request switch 126.

Figure 4:
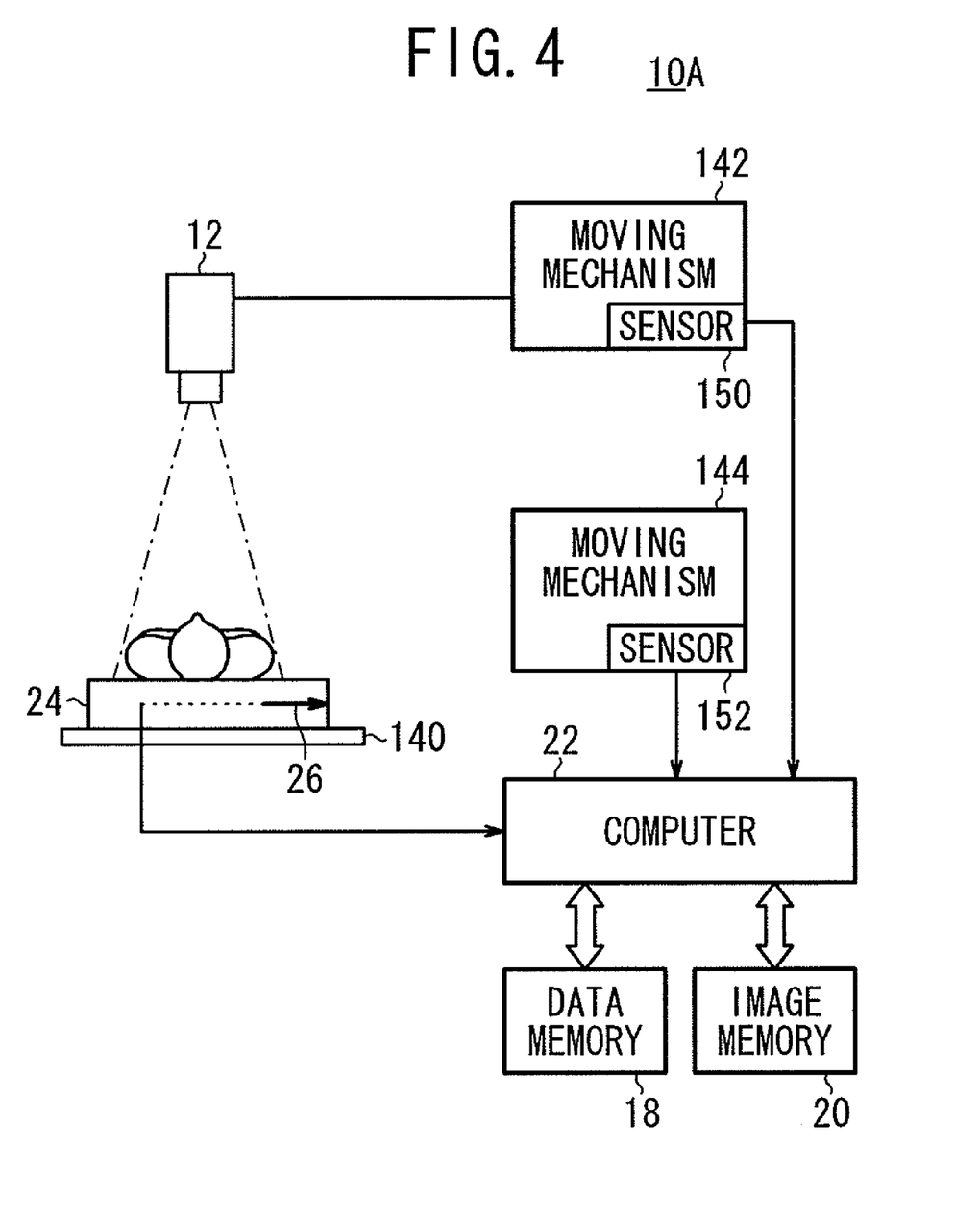
FIG. 4 is a block diagram of the first radiation image capturing apparatus, which is arranged to operate in a second mode.

The first radiation image capturing apparatus 10A can be operated selectively in a first mode or in a second mode. In the first mode, the subject 14 is imaged while in an upstanding position. In the second mode, the subject 14 is imaged while lying down. According to the first mode, as shown in FIG. 1, the cassette 24 is mounted on an image capturing base 140, which is held in an upright position with the image capturing surface, i.e., the image capturing surface of the radiation conversion panel 16 thereof, extending vertically. The subject 14 stands in facing relation to the image capturing surface of the cassette 24 mounted on the image capturing base 140, and the radiation source 12 is placed in confronting relation to the subject 14. The radiation source 12 and the image capturing base 140 are movable horizontally toward and away from each other by respective moving mechanisms 142, 144, which are of a known configuration. According to the second mode, as shown in FIG. 4, the subject 14 lies on a top plate (not shown), and the cassette 24 is set on the image capturing base 140 disposed below the top plate. The top plate is positioned in facing relation to the image capturing surface of the cassette 24, and the radiation source 12 is placed in confronting relation to the top plate. The radiation source 12 and the image capturing base 140 also are movable vertically toward and away from each other by respective moving mechanisms 142, 144, which are of a known configuration.

The distance measuring unit 106 has a first position sensor 150, such as a rotary encoder or the like, for measuring the distance that the radiation source 12 has moved, and a second position sensor 152, such as a rotary encoder or the like, for measuring the distance that the image capturing base 140 has moved. The distance measuring unit 106 measures the second distance from the radiation source 12 to the radiation conversion panel 16, based on the detected values from the first position sensor 150 and the second position sensor 152.

The first radiation field calculating unit 108 calculates a radiation field at the position of the radiation conversion panel 16, based on setting information representative of the type and aperture of the radiation source 12 taken from among the setting information of the radiation source 12 that is registered in the data memory 18, and the second distance from the distance measuring unit 106. The calculated radiation field differs depending on the shape of the radiation field. If the shape of the radiation field is circular, then the first radiation field calculating unit 108 determines a diameter thereof. If the shape of the radiation field is elliptical, then the first radiation field calculating unit 108 determines major and minor axes thereof. If the shape of the radiation field is polygonal, such as triangular, rectangular, or the like, then the first radiation field calculating unit 108 determines an area thereof.

Herein, for the sake of brevity, it shall be assumed that the shape of the radiation field is circular.

The first radiation field calculating unit 108 calculates a diameter (first diameter) of a radiation field at the position of the radiation conversion panel 16, based on the setting information representative of the type and aperture of the radiation source 12, and the second distance from the distance measuring unit 106. The second radiation field calculating unit 110 determines a diameter (second diameter) of a hypothetical radiation field at the reference position of the subject 14, based on the setting information representative of the type and aperture of the radiation source 12, the second distance from the distance measuring unit 106, and the first distance from the input device 104.

The life-size correcting unit 114 calculates a reduction ratio for the radiation image information acquired from the radiation conversion panel 16, based on the radiation field (the first diameter) from the first radiation field calculating unit 108, and the hypothetical radiation field (the second diameter) from the second radiation field calculating unit 110. The reduction ratio can be determined according to the following equation:

Reduction ratio=second diameter/first diameter

The life-size correcting unit 114 then multiplies the vertical and horizontal sizes of the radiation image information by the reduction ratio in order to produce the life-sized image information.

The life-sized image information at the reference position of the subject 14 is output from the second output unit 122 to the printer 116, which produces a hard copy of the life-sized image information. Alternatively, the life-sized image information is output from the second output unit 122 to the display monitor 118, which displays the life-sized image information.

Operations of the first radiation image capturing apparatus 10A will be described below.

First, the cassette 24 is set on the image capturing base 140, the subject 14 is positioned in facing relation to the image capturing surface of the cassette 24, and the radiation source 12 is placed in confronting relation to the subject 14.

The doctor or a radiological technician (hereinafter referred to as an "operator") in charge of the subject 14 inputs the type, aperture, etc., of the radiation source 12 through the input device 104 to the computer 22, which registers the input data in the data memory 18. Then, the operator operates the default value setting switch 124 to display a setting screen on the display monitor 118. Thereafter, the operator measures the first distance from the marker 26 on the side wall of the casing of the cassette 24 to the reference position of the subject 14, for example, a position corresponding to the shoulder bone of the subject 14, and inputs the first distance to the input device 104. The information of the first distance is stored as a default value in the data memory 18 by the first distance storage unit 132.

Then, the operator operates a radiation applying switch to capture a radiation image of the subject 14. Radiation emitted from the radiation source 12 and having passed through the subject 14 is converted by the radiation conversion panel 16 into radiation image information, which is read by the computer 22 and stored in the first memory area 100 of the image memory 20. At this time, the distance measuring unit 106 measures the second distance from the radiation source 12 to the radiation conversion panel 16, and the first radiation field calculating unit 108 determines a first radiation field (first diameter) at the position of the radiation conversion panel 16, based on the setting information of the radiation source 12 and the second distance.

Normally, radiation image information read from the first memory area 100 of the image memory 20 is output from the first output unit 120 to the printer 116 or to the display monitor 118.

According to the present embodiment, when the operator operates the correction execution switch 128, the second radiation field calculating unit 110 reads the first distance from the data memory 18, and determines a hypothetical radiation field at the reference position of the subject 14 based on the setting information of the radiation source 12, the second distance, and the first distance. The life-size correcting unit 114 reads the radiation image information from the image memory 20, and corrects the radiation image information to provide life-sized image information, based on the information of the calculated radiation field and the information of the calculated hypothetical radiation field. The life-sized image information is stored in the second memory area 112 of the image memory 20.

The life-sized image information that is stored in the second memory area 112 of the image memory 20 is output from the first output unit 120 to the printer 116 or to the display monitor 118.

As described thus far, life-sized image information has been obtained based on the first distance, which is input before the radiation image information is captured, e.g., the first distance from the marker 26 to the reference position at the shoulder bone of the subject 14.

The life-sized image information thus generated is based on a position corresponding to the first distance that is input through the input device 104, e.g., the position at the shoulder bone of the subject 14. Therefore, an image of another region of the subject 14, which is closer to the cassette 24 from the reference position, is captured in a size smaller than its actual size, whereas an image of another region of the subject 14, which is closer to the radiation source 12 from the reference position, is captured in a size greater than its actual size. The relative positions of these regions from the reference position remain essentially the same for different subjects 14.

According to the first radiation image capturing apparatus 10A, the operator operates the correction request switch 126 in order to change the first distance for thereby obtaining life-sized image information of the above regions. At times that second and subsequent correction requests are made, the operator inputs the first distances corresponding to the above regions on the setting screen that is displayed on the display monitor 118, and operates the correction execution switch 128. Therefore, the printer 116 or the monitor 118 produces or displays life-sized image information of the above regions. Consequently, the first radiation image capturing apparatus 10A can easily produce life-sized images of regions other than the reference position, thus enabling the operator to confirm such regions quickly during medical procedures.

Since the first radiation image capturing apparatus 10A can easily produce life-sized image information at any arbitrary position from the radiation conversion panel 16 based on the radiation image information that already has been acquired, medical procedures performed using the radiation image capturing apparatus can effectively be shortened.

As described above, although the image corresponding to the reference position is corrected to provide a life-sized image, images of the other regions are produced in sizes that differ from the actual size of the subject. If the operator is not certain as to whether the image displayed on the display monitor 118 has been converted into a life-sized image or not, then the operator might possibly misidentify the size and position of the region of the subject 14 in question (i.e., currently under investigation).

Figure 5:
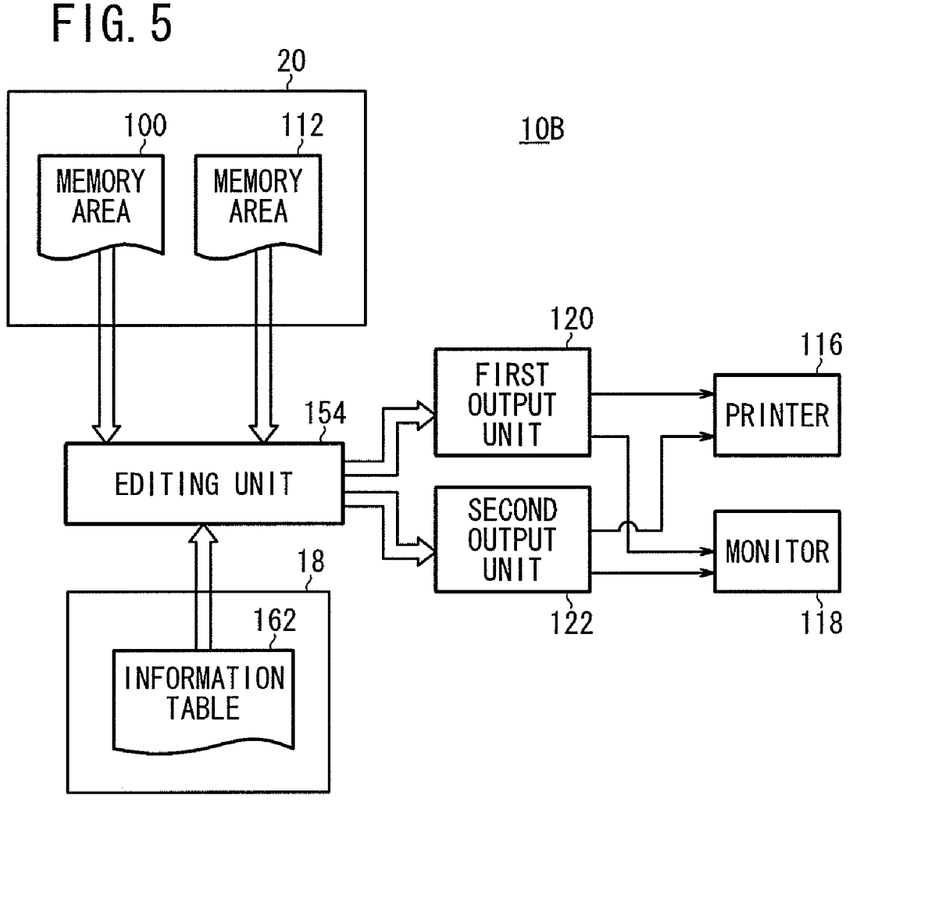
FIG. 5 is a functional block diagram of a characteristic section of a second radiation image capturing apparatus according to the present invention.

FIG. 5 shows a radiation image capturing apparatus 10B according to a second embodiment of the present invention (hereinafter referred to as "second radiation image capturing apparatus 10B"). When the second radiation image capturing apparatus 10B displays a radiation image on the display monitor 118, the second radiation image capturing apparatus 10B also displays, in a marginal space of the radiation image, a message indicating whether the radiation image has been corrected to provide a life-sized representation or not. If the radiation image has been converted into a life-sized image, the second radiation image capturing apparatus 10B further displays the value of the first distance as well as region information (e.g., the name of a region such as "shoulder bone" or the like), which corresponds to the reference position of the subject 14.

Figure 6A:
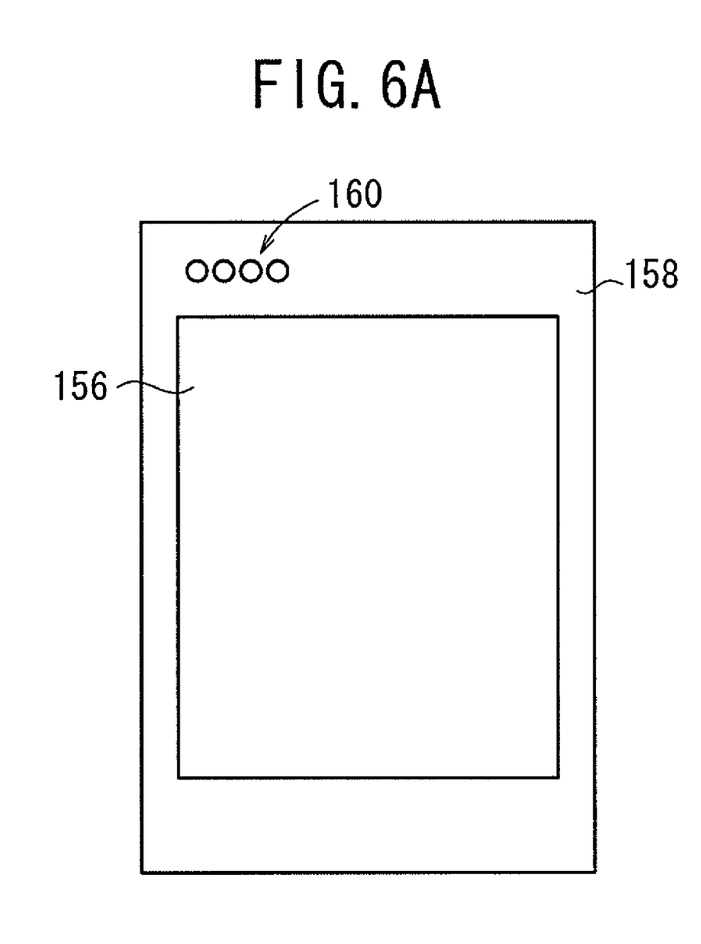
FIG. 6A is a diagram showing a radiation image, including a marginal space where a message indicating that the radiation image has not been converted into a life-sized image is displayed.

As shown in FIG. 5, the second radiation image capturing apparatus 10B includes an editing unit 154 in a characteristic section thereof. The editing unit 154 adds information made up of a message, which indicates that the radiation image has not been corrected to provide a life-sized image, to the radiation image information read from the first memory area 100 of the image memory 20. The radiation image information, to which the message information has been added, is output from the first output unit 120 to the printer 116 or to the display monitor 118. As shown in FIG. 6A, a radiation image 156 is displayed on the display monitor 118 based on the supplied radiation information, wherein the radiation image 156 includes a marginal space 158 where a message 160 is displayed indicating that the radiation image has not been corrected to provide a life-sized representation.

The editing unit 154 also adds at least one of the message information indicating that the radiation image has been corrected (converted) into a life-sized representation, the value of the first distance based on which the radiation image has been corrected, and the region information corresponding to the reference position of the subject 14, i.e., the reference position determined by the first distance. In this case, such information is added to the life-sized image information, which is read from the second memory area 112 of the image memory 20. The first distance is read from the data memory 18 and added to the life-sized image information. For adding the region information, an information table 162 (see FIG. 5) is prepared, which indicates a relationship between information concerning the first distance and the name of the region. The information concerning the first distance represents a default value of the first distance, i.e., the distance to the position of the shoulder bone, or a relative distance from the default value to a first distance, which may be subsequently input arbitrarily. The name "shoulder bone" is assigned to the default value. If the read first distance is the default value, then the editing unit 154 reads the region information corresponding to the first distance, and then adds the region information to the life-sized image information.

Figure 6B:
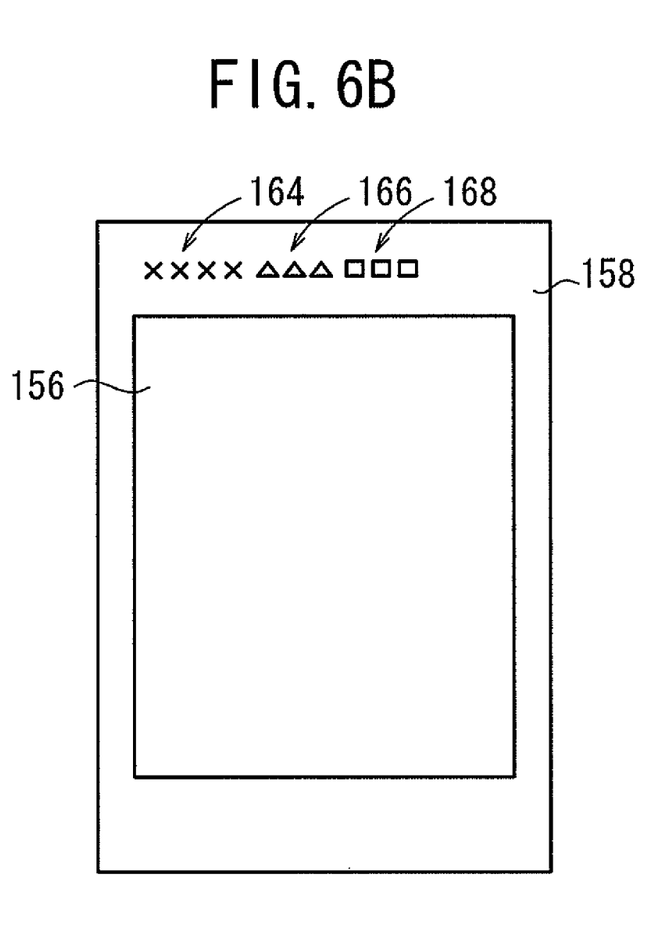
FIG. 6B is a diagram showing a radiation image including a marginal space where a message indicating that the radiation image has been converted into a life-sized image is displayed, while also indicating the value of a first distance, and the name of a region.

The life-sized image information edited by the editing unit 154 is output from the second output unit 122 to the printer 116 or to the display monitor 118. As shown in FIG. 6B, a radiation image 156 displayed on the display monitor 118 based on the supplied life-sized image information includes a marginal space 158 therein, where a message 164 indicating that the radiation image has been corrected to provide a life-sized representation, a value 166 of the first distance, and a region name 168 are displayed. At least one of the message 164, the value 166 of the first distance, and the region name 168 may be displayed in the marginal space 158.

Therefore, the operator can recognize at a glance whether the image displayed on the display monitor 118 is an image taken directly from the radiation conversion panel 16, or an image that has been corrected (converted) into a life-sized image. If the displayed image is an image that has been corrected to provide a life-sized representation, then the operator also can recognize at a glance which region of the subject 14 is represented by the displayed life-sized image. The operator thus is prevented from misidentifying the size and position of the region of the subject 14 in question.

Figure 7:
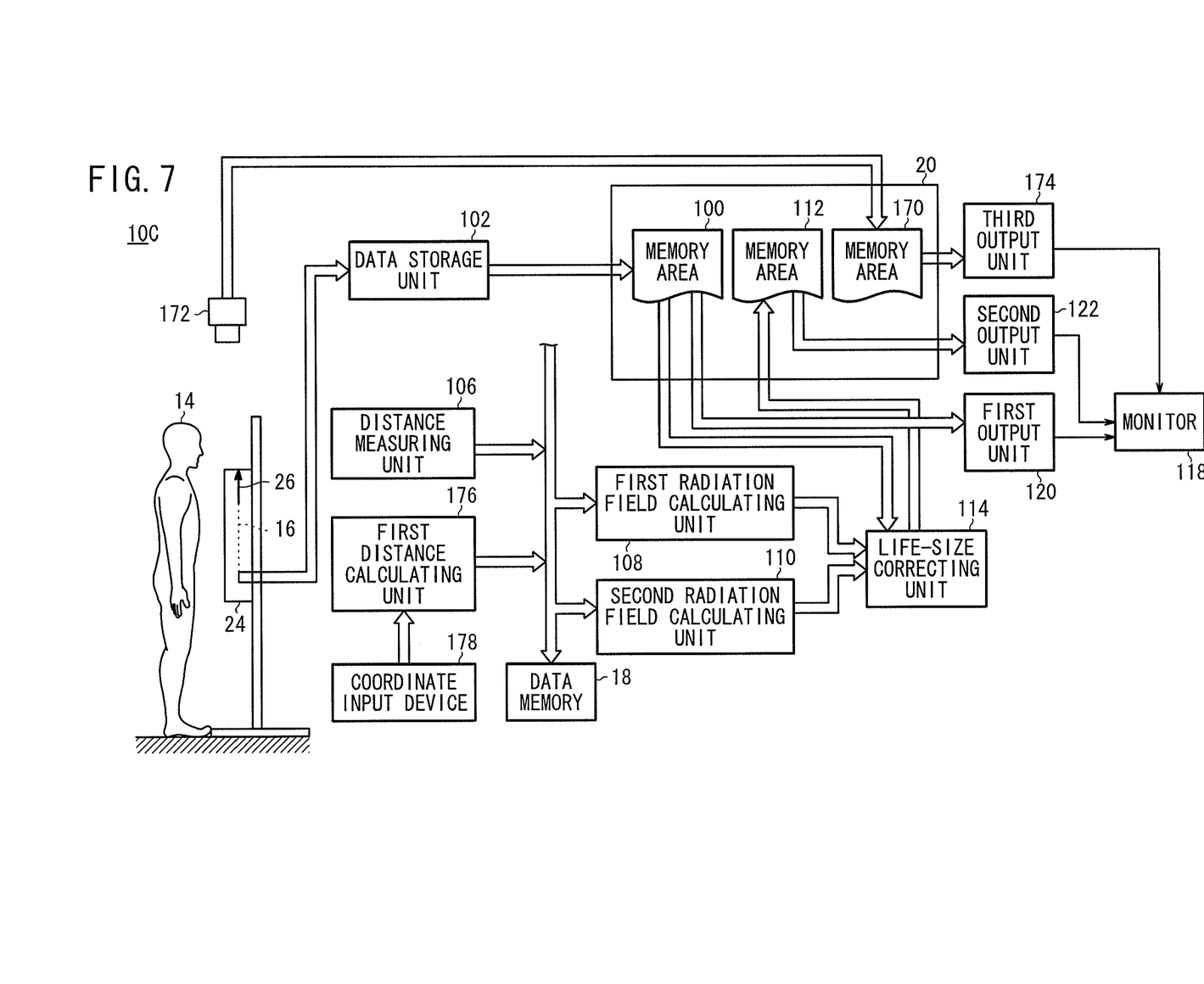
FIG. 7 is a functional block diagram of a control system of a third radiation image capturing apparatus according to the present invention.

FIG. 7 shows a radiation image capturing apparatus 10C according to a third embodiment of the present invention (hereinafter referred to as "third radiation image capturing apparatus 10C"). As shown in FIG. 7, the third radiation image capturing apparatus 10C includes an image capturing unit 172 for capturing an image both of the cassette 24 and the subject 14, and storing the captured image information in a third memory area 170 of the image memory 20. The third radiation image capturing apparatus 10C further includes a third output unit 174 for reading the captured image information from the third memory area 170 of the image memory 20 and displaying the image on the display monitor 118, and a first distance calculating unit 176 for calculating a first distance based on the captured image information from the image capturing unit 172. The image capturing unit 172 preferably comprises a digital camera.

Preferably, the image capturing unit 172 is located at a position where it can capture an image showing both the side wall of the cassette 24 on which the marker 26 is placed, together with the side of the subject 14.

Before a radiation image of the subject 14 is captured, both the cassette 24 and the subject 14 are imaged and captured image information therefrom is displayed on the display monitor 118. Using a coordinate input device 178 such as a mouse or the like, the operator designates the image of the marker 26 on the side wall of the cassette 24, along with the image of the region of the subject 14, which may correspond to the shoulder bone, for example. The first distance calculating unit 176 then calculates the actual first distance from the marker 26 on the side wall of the cassette 24 to the region of the subject 14 corresponding to the shoulder bone, based on the input coordinate data and the magnification or reduction ratio of the captured image information. The calculated first distance is stored as a default value in the data memory 18.

Other operational details of the radiation image capturing apparatus 10C are the same as those of the radiation image capturing apparatus 10A, and hence will not be described in detail below.

The radiation image capturing apparatus 10C does not require the operator to actually measure the first distance with a measuring rule or the like. Rather, the first distance can easily be input by the image capturing unit 172, such as a digital camera or the like. Accordingly, the radiation image capturing apparatus 10C has a shortened operating cycle.

Figure 8:
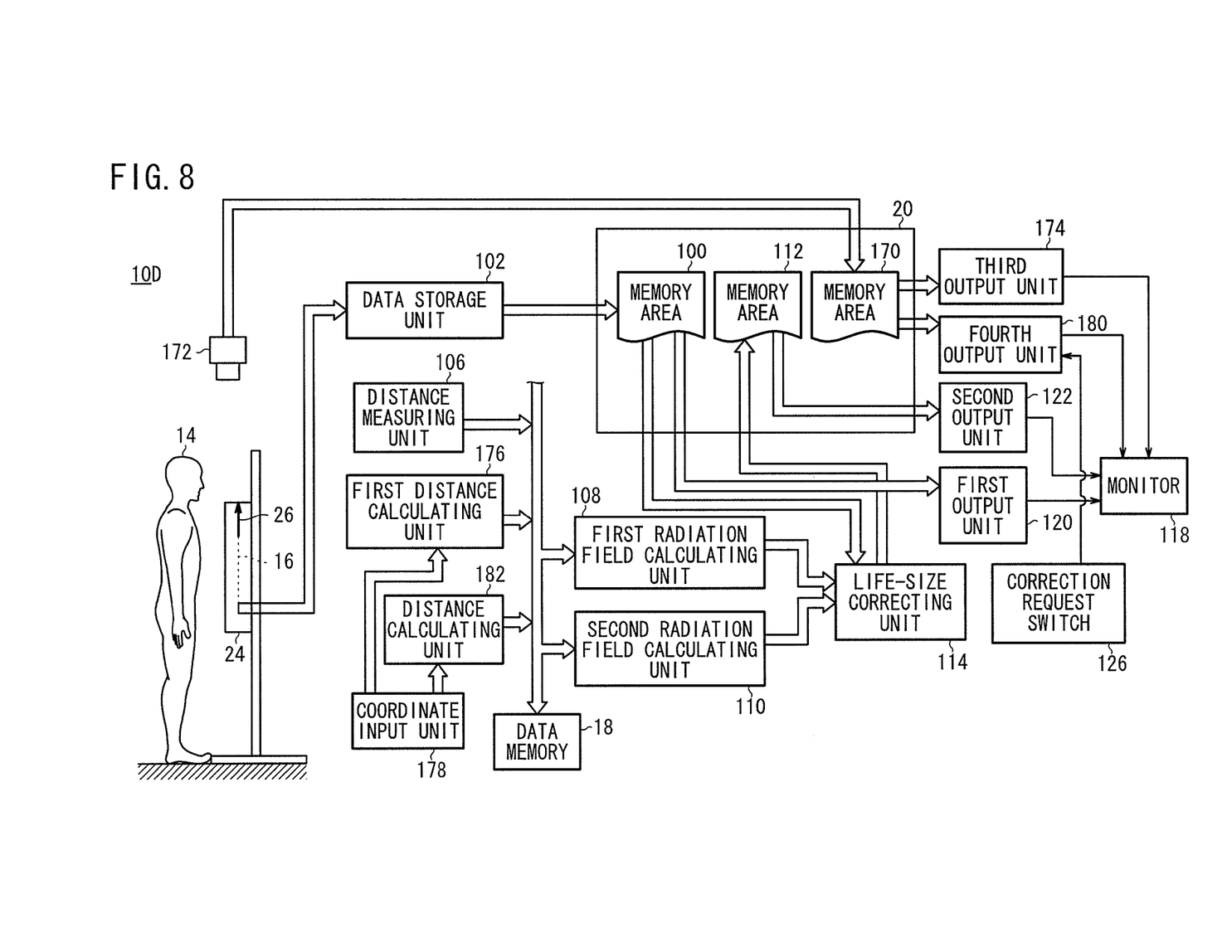
FIG. 8 is a functional block diagram of a control system of a fourth radiation image capturing apparatus according to the present invention.

FIG. 8 shows a radiation image capturing apparatus 10D according to a fourth embodiment of the present invention (hereinafter referred to as "fourth radiation image capturing apparatus 10D").

As shown in FIG. 8, the fourth radiation image capturing apparatus 10D uses the image captured by the image capturing unit 172 for obtaining life-sized images of various regions of the subject 14.

When the operator operates the correction request switch 126 on the control console, the display monitor 118 displays an image based on the captured image information stored in the third memory area 170 of the image memory 20. Using the coordinate input device 178, the operator designates the image of the marker 26 on the side wall of the cassette 24 and the image of an arbitrary region of the subject 14. Then, the first distance is calculated and stored in the data memory 18.

Specifically, the fourth radiation image capturing apparatus 10D includes a fourth output unit 180 for reading captured image information from the third memory area 170 of the image memory 20, and for displaying an image on the display monitor 118 based on the image information in response to operation of the correction request switch 126. The fourth radiation image capturing apparatus 10D further comprises a distance calculating unit 182 for reading coordinate data from the coordinate input device 178, calculating the first distance, and storing the first distance in the data memory 18.

After the first distance has been automatically calculated based on the coordinate data input from the coordinate input device 178, the operator operates the correction execution switch 128 in order to output life-sized image information of the region depending on the first distance to the printer 116 or to the display monitor 118.

Since the fourth radiation image capturing apparatus 10D automatically calculates the first distance based on the image information captured by the image capturing unit 172 and the coordinate data entered via a GUI (Graphic User Interface) after the radiation image information has been captured, the fourth radiation image capturing apparatus 10D allows the operator to easily confirm life-sized images taken from various regions of the subject 14. Accordingly, the fourth radiation image capturing apparatus 10D serves as a time saver.

Figure 9:
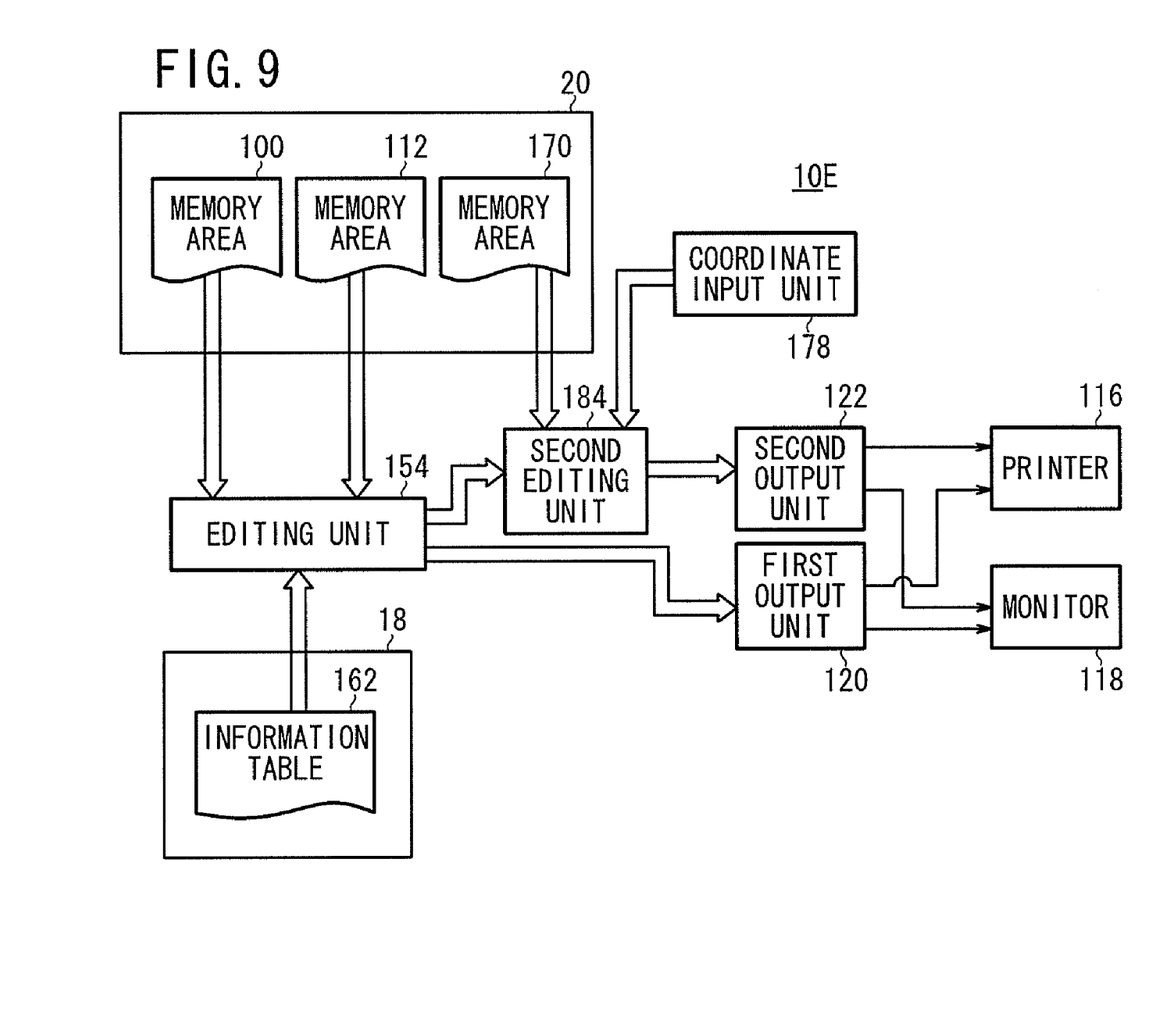
FIG. 9 is a functional block diagram of a characteristic section of a fifth radiation image capturing apparatus according to the present invention.

FIG. 9 shows a radiation image capturing apparatus 10E according to a fifth embodiment of the present invention (hereinafter referred to as "fifth radiation image capturing apparatus 10E").

As shown in FIG. 9, the fifth radiation image capturing apparatus 10E is of essentially the same arrangement as the second radiation image capturing apparatus 10B, but differs therefrom in that it includes a second editing unit 184.

The second editing unit 184 reads the captured image information from the third memory area 170 of the image memory 20, and plots a marker 186 (see FIG. 10) at a position corresponding to the image of a region that is designated by the coordinate input device 178. The second editing unit 184 then reduces the size of the captured image information with the marker 186 plotted therein, and adds the reduced-sized image information to the life-sized radiation image 156.

Figure 10:
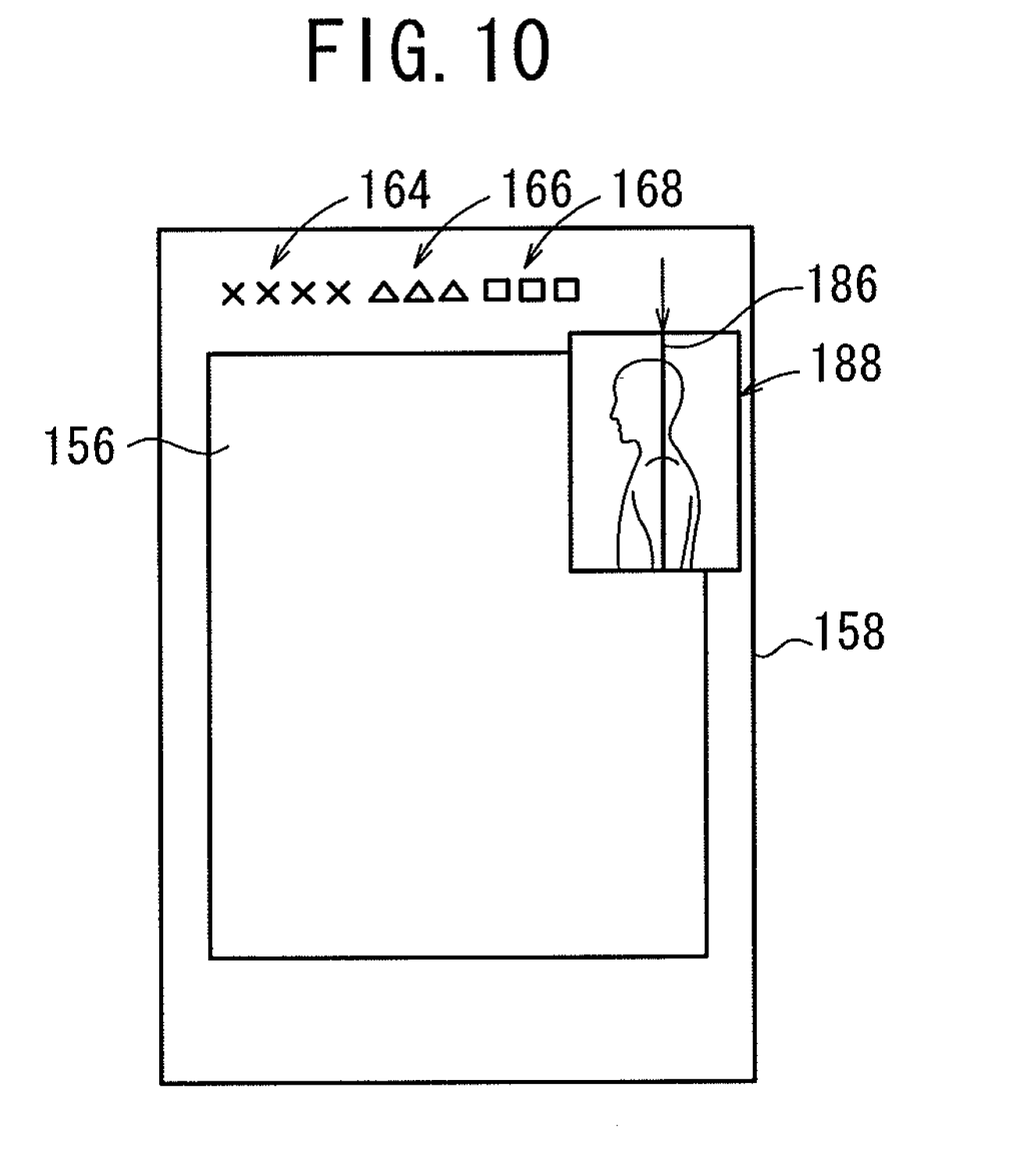
FIG. 10 is a diagram showing a radiation image combined with an additional displayed image of captured information with a marker displayed thereon.

Specifically, as shown in FIG. 10, to the life-sized radiation image 156 displayed on the display monitor 118, there are added the message 164 indicating that the radiation image has been corrected (converted) into a life-sized image, the value 166 of the first distance, the region name 168, and a reduced image 188 representative of the captured image information, with the marker 186 plotted therein by the second editing unit 184. Alternatively, at least one of the message 164, the value 166 of the first distance, the region name 168, and the reduced image 188 representative of the captured image information along with the marker 186 plotted therein may be displayed in addition to the life-sized radiation image 156.

The fifth radiation image capturing apparatus 10E allows the operator to recognize at a glance whether the image displayed on the display monitor 118 is an image taken directly from the radiation conversion panel 16, or an image that has been corrected to provide a life-sized representation. If the displayed image is an image that has been corrected to provide a life-sized representation, then the operator can also recognize at a glance which region of the subject 14 is represented by the displayed life-sized image. The operator therefore is prevented from misidentifying the size and position of the region of the subject 14 in question.

The radiation conversion panel 16 used in the first radiation image capturing apparatus 10A through the fifth radiation image capturing apparatus 10E described above converts the incident radiation directly into an electrical signal corresponding to the amount of the radiation by means of the photoelectric conversion layer 51 (i.e., direct conversion type). Instead, the radiation conversion panel may, however, convert the incident radiation into visible light with a scintillator and then the visible light into an electrical signal using solid-state detecting elements such as a-Si (i.e., indirect conversion type, see Japanese Patent No. 3494683).

The radiation image information may also be acquired with light readout type radiation conversion panels. In light readout type radiation conversion panels, a two-dimensional array of solid-state detecting elements receives radiation and stores an electrostatic latent image corresponding to the amount of radiation. Readout of the latent image is carried out by applying reading light onto the radiation conversion panel and utilizing the value of the electrical current generated by the radiation conversion panel as radiation image information. After reading out the radiation image information, the latent image and the radiation image information of the radiation conversion panel can be erased by irradiating the radiation conversion panel with erasing light, so that the radiation conversion panel can be reused (see Japanese Laid-Open Patent Publication No. 2000-105297).

While the radiation conversion panel 16 of the radiation image capturing apparatus 10 utilizes the thin-film transistors (TFTs) 52 in the above-mentioned embodiments, such a device as a CCD (Charge Coupled Device), a CMOS (Complementary Metal Oxide Semiconductor) device or the like may also be used instead of the TFTs 52.

Although certain preferred embodiments of the present invention have been shown and described in detail, it should be understood that various changes and modifications may be made to the embodiments without departing from the scope of the invention as set forth in the appended claims.

What is claimed is:

1. A radiation image capturing apparatus comprising:
   a radiation source;
   a radiation conversion panel for detecting radiation emitted from the radiation source, and which has passed through a subject, and converting the detected radiation into radiation image information;
   an input device for inputting at least a first distance from a position of the radiation conversion panel to a position serving as a reference position for the subject;
   a distance measuring unit for measuring a second distance from the radiation source to the radiation conversion panel;
   a first radiation field calculating unit for determining a radiation field at the position of the radiation conversion panel based on setting information of the radiation source and the second distance;
   a second radiation field calculating unit for determining a hypothetical radiation field at the reference position of the subject based on the setting information of the radiation source, the first distance, and the second distance; and
   a life-size correcting unit for correcting the radiation image information from the radiation conversion panel to provide life-sized image information based on the information of the calculated radiation field and the information of the determined hypothetical radiation field.

2. A radiation image capturing apparatus according to claim 1, further comprising an output unit for outputting the life-sized image information from the life-size correcting unit.

3. A radiation image capturing apparatus according to claim 1, further comprising:
   an editing unit for editing at least one of message information indicating that the radiation image information has been corrected to provide the life-sized image information from the life-size correcting unit, the information of the first distance, and information indicative of the reference position of the subject, to thereby provide edited image information; and
   an output unit for outputting the edited image information from the editing unit.

4. A radiation image capturing apparatus according to claim 1, wherein the input device comprises:
   an image capturing unit for capturing an image of the radiation conversion panel and the subject; and
   a distance calculating unit for calculating the first distance based on captured image information from the image capturing unit.

5. A radiation image capturing apparatus according to claim 1, further comprising:
   an image capturing unit for capturing an image of the radiation conversion panel and the subject;
   a marker adding unit for adding marker information indicative of the position serving as the reference position of the subject, which is spaced from the position of the radiation conversion panel by the first distance, the marker information being added to captured image information from the image capturing unit;
   an editing unit for editing at least one of message information indicating that the radiation image information has been corrected to provide the life-sized image information from the life-size correcting unit, the information of the first distance, information indicative of the reference position of the subject, and the captured image information to which the marker information has been added, to thereby provide edited image information; and
   an output unit for outputting the edited image; information from the editing unit.

6. A radiation image capturing apparatus according to claim 1, further comprising a cassette having a casing, the radiation conversion panel being housed in the casing, the casing including a side wall bearing thereon a marker indicative of an installation position of the radiation conversion panel.

* * * * *

UNITED STATES PATENT AND TRADEMARK OFFICE
CERTIFICATE OF CORRECTION

PATENT NO. : 7,729,475 B2  
APPLICATION NO. : 12/239273  
DATED : June 1, 2010  
INVENTOR(S) : Eiichi Kito et al.

It is certified that error appears in the above-identified patent and that said Letters Patent is hereby corrected as shown below:

Title Page, Item (30) Foreign Application Priority Data delete "2007-2551330" and insert --2007-255133--.

Signed and Sealed this

Sixteenth Day of November, 2010

David J. Kappos  
*Director of the United States Patent and Trademark Office*